(12) United States Patent
Palushi et al.

(10) Patent No.: US 10,485,609 B2
(45) Date of Patent: Nov. 26, 2019

(54) DILATION BALLOON WITH RF ENERGY DELIVERY FEATURE

(71) Applicant: Acclarent, Inc., Irvine, CA (US)

(72) Inventors: Jetmir Palushi, Irvine, CA (US); Ketan P. Muni, San Jose, CA (US)

(73) Assignee: Acclarent, Inc., Irvine, CA (US)

( * ) Notice: Subject to any disclaimer, the term of this patent is extended or adjusted under 35 U.S.C. 154(b) by 459 days.

(21) Appl. No.: 15/296,274

(22) Filed: Oct. 18, 2016

(65) Prior Publication Data

US 2018/0104001 A1 Apr. 19, 2018

(51) Int. Cl.
| | |
|---|---|
| *A61B 18/12* | (2006.01) |
| *A61B 18/14* | (2006.01) |
| *A61B 1/00* | (2006.01) |
| *A61B 1/233* | (2006.01) |
| *A61M 25/00* | (2006.01) |
| *A61B 18/00* | (2006.01) |

(52) U.S. Cl.
CPC ...... *A61B 18/1492* (2013.01); *A61B 1/00183* (2013.01); *A61B 1/233* (2013.01); *A61B 18/1206* (2013.01); *A61M 25/00* (2013.01); *A61B 2018/0016* (2013.01); *A61B 2018/0022* (2013.01); *A61B 2018/00077* (2013.01); *A61B 2018/00083* (2013.01); *A61B 2018/00244* (2013.01); *A61B 2018/00267* (2013.01); *A61B 2018/00327* (2013.01); *A61B 2018/00577* (2013.01); *A61B 2018/00589* (2013.01); *A61B 2018/00613* (2013.01); *A61B 2018/126* (2013.01); *A61B 2018/144* (2013.01)

(58) Field of Classification Search
CPC .......... A61B 1/233; A61B 2018/00077; A61B 2018/00083; A61B 2018/0016; A61B 2018/0022; A61B 2018/00244; A61B 2018/00267; A61B 2018/00327; A61B 2018/126

See application file for complete search history.

(56) References Cited

U.S. PATENT DOCUMENTS

| | | | | |
|---|---|---|---|---|
| 4,362,150 | A * | 12/1982 | Lombardi, Jr. | ............................ A61M 25/10184 600/18 |
| 6,033,397 | A * | 3/2000 | Laufer | ................... A61B 18/08 604/105 |
| 6,036,689 | A * | 3/2000 | Tu | ...................... A61B 18/1492 604/103.08 |
| 6,322,559 | B1 * | 11/2001 | Daulton | ............. A61B 18/1492 606/41 |

(Continued)

OTHER PUBLICATIONS

International Search Report and Written Opinion dated Jan. 4, 2018 for Application No. PCT/US2017/055691, 12 pgs.

*Primary Examiner* — Daniel W Fowler
(74) *Attorney, Agent, or Firm* — Frost Brown Todd LLC

(57) ABSTRACT

An apparatus includes a shaft, an expandable dilator, and a wire assembly. The expandable dilator is located at the distal end of the shaft. The expandable dilator is operable to transition between a non-expanded configuration and an expanded configuration. The wire assembly is disposed about an exterior of the expandable dilator. The proximal end of the wire assembly is proximal to the proximal end of the expandable dilator. The distal end of the wire assembly is distal to the distal end of the dilator. The wire assembly is configured to apply bipolar RF energy to tissue.

20 Claims, 12 Drawing Sheets

(56) References Cited

U.S. PATENT DOCUMENTS

| | | |
|---|---|---|
| 7,462,175 B2 | 12/2008 | Chang et al. |
| 7,630,676 B2 | 12/2009 | Pirwitz |
| 7,720,521 B2 | 5/2010 | Chang et al. |
| 8,123,722 B2 | 2/2012 | Chang et al. |
| 8,190,389 B2 | 5/2012 | Kim et al. |
| 8,320,711 B2 | 11/2012 | Altmann et al. |
| 8,702,626 B1 | 4/2014 | Kim et al. |
| 8,900,227 B2 | 12/2014 | Stierman |
| 8,936,594 B2 | 1/2015 | Wolf et al. |
| 9,155,492 B2 | 10/2015 | Jenkins et al. |
| 9,167,961 B2 | 10/2015 | Makower et al. |
| 9,198,736 B2 | 12/2015 | Kim et al. |
| 9,314,208 B1 * | 4/2016 | Altmann .............. A61B 5/6858 |
| 2007/0208252 A1 | 9/2007 | Makower |
| 2008/0183128 A1 | 7/2008 | Morriss et al. |
| 2010/0030031 A1 | 2/2010 | Goldfarb et al. |
| 2011/0004057 A1 | 1/2011 | Goldfarb et al. |
| 2011/0060214 A1 | 3/2011 | Makower |
| 2014/0074141 A1 | 3/2014 | Johnson et al. |
| 2014/0200444 A1 | 7/2014 | Kim et al. |
| 2014/0364725 A1 | 12/2014 | Makower |
| 2015/0045787 A1 * | 2/2015 | Bloom ............... A61B 18/1492 606/41 |
| 2016/0008083 A1 | 1/2016 | Kesten et al. |
| 2016/0113709 A1 * | 4/2016 | Maor ................ A61B 18/1492 606/41 |
| 2016/0310042 A1 | 10/2016 | Kesten et al. |
| 2016/0331459 A1 * | 11/2016 | Townley ................ A61N 7/00 |

\* cited by examiner

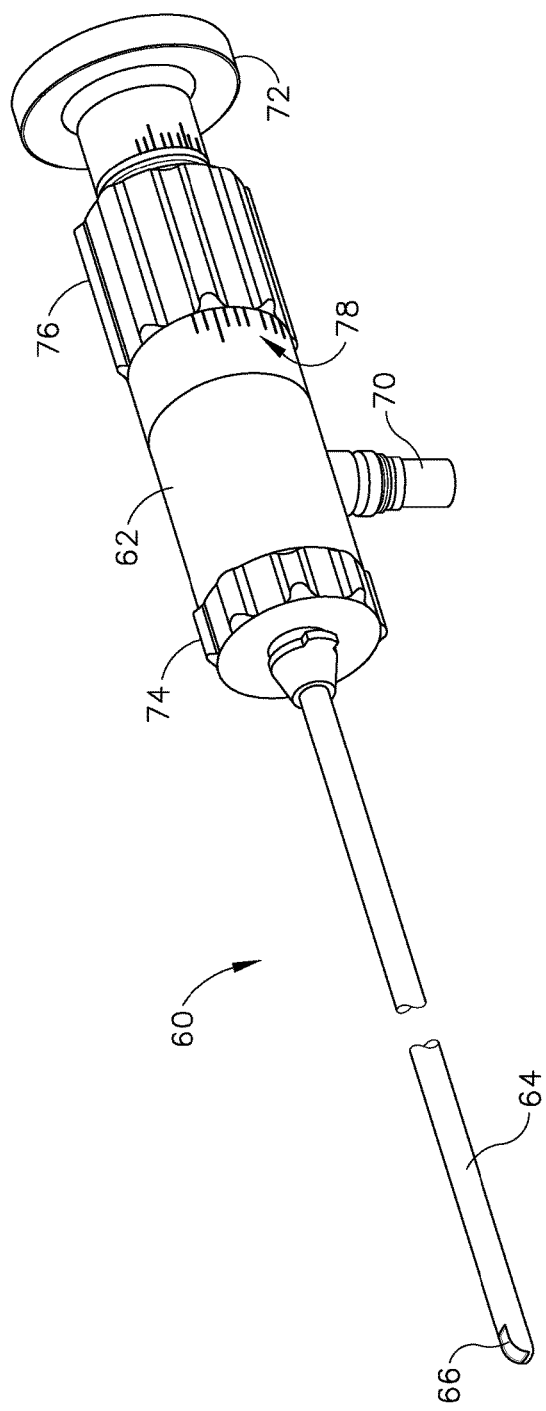
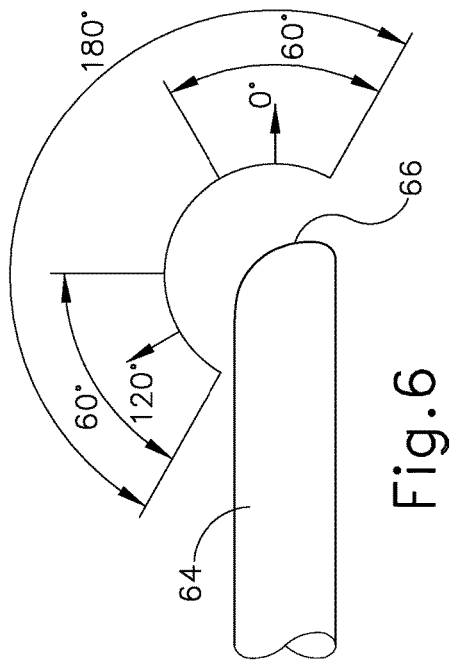
Fig.5
Fig.6

DILATION BALLOON WITH RF ENERGY DELIVERY FEATURE

BACKGROUND

In some instances, it may be desirable to dilate an anatomical passageway in a patient. This may include dilation of ostia of paranasal sinuses (e.g., to treat sinusitis), dilation of the larynx, dilation of the Eustachian tube, dilation of other passageways within the ear, nose, or throat, etc. One method of dilating anatomical passageways includes using a guide wire and catheter to position an inflatable balloon within the anatomical passageway, then inflating the balloon with a fluid (e.g., saline) to dilate the anatomical passageway. For instance, the expandable balloon may be positioned within an ostium at a paranasal sinus and then be inflated, to thereby dilate the ostium by remodeling the bone adjacent to the ostium, without requiring incision of the mucosa or removal of any bone. The dilated ostium may then allow for improved drainage from and ventilation of the affected paranasal sinus. A system that may be used to perform such procedures may be provided in accordance with the teachings of U.S. Pub. No. 2011/0004057, entitled "Systems and Methods for Transnasal Dilation of Passageways in the Ear, Nose or Throat," published Jan. 6, 2011, now abandoned, the disclosure of which is incorporated by reference herein. An example of such a system is the Relieva® Spin Balloon Sinuplasty™ System by Acclarent, Inc. of Menlo Park, Calif.

A variable direction view endoscope may be used with such a system to provide visualization within the anatomical passageway (e.g., the ear, nose, throat, paranasal sinuses, etc.) to position the balloon at desired locations. A variable direction view endoscope may enable viewing along a variety of transverse viewing angles without having to flex the shaft of the endoscope within the anatomical passageway. Such an endoscope that may be provided in accordance with the teachings of U.S. Pub. No. 2010/0030031, entitled "Swing Prism Endoscope," published Feb. 4, 2010, now abandoned, the disclosure of which is incorporated by reference herein. An example of such an endoscope is the Acclarent Cyclops™ Multi-Angle Endoscope by Acclarent, Inc. of Menlo Park, Calif.

While a variable direction view endoscope may be used to provide visualization within the anatomical passageway, it may also be desirable to provide additional visual confirmation of the proper positioning of the balloon before inflating the balloon. This may be done using an illuminating guidewire. Such a guidewire may be positioned within the target area and then illuminated, with light projecting from the distal end of the guidewire. This light may illuminate the adjacent tissue (e.g., hypodermis, subdermis, etc.) and thus be visible to the naked eye from outside the patient through transcutaneous illumination. For instance, when the distal end is positioned in the maxillary sinus, the light may be visible through the patient's cheek. Using such external visualization to confirm the position of the guidewire, the balloon may then be advanced distally along the guidewire into position at the dilation site. Such an illuminating guidewire may be provided in accordance with the teachings of U.S. Pub. No. 2012/0078118, entitled "Sinus Illumination Lightwire Device," published Mar. 29, 2012, issued as U.S. Pat. No. 9,155,492 on Oct. 13, 2015, the disclosure of which is incorporated by reference herein. An example of such an illuminating guidewire is the Relieva Luma Sentry™ Sinus Illumination System by Acclarent, Inc. of Menlo Park, Calif.

Image-guided surgery (IGS) is a technique where a computer is used to obtain a real-time correlation of the location of an instrument that has been inserted into a patient's body to a set of preoperatively obtained images (e.g., a CT or MRI scan, 3-D map, etc.) so as to superimpose the current location of the instrument on the preoperatively obtained images. In some IGS procedures, a digital tomographic scan (e.g., CT or MRI, 3-D map, etc.) of the operative field is obtained prior to surgery. A specially programmed computer is then used to convert the digital tomographic scan data into a digital map. During surgery, special instruments having sensors (e.g., electromagnetic coils that emit electromagnetic fields and/or are responsive to externally generated electromagnetic fields) mounted thereon are used to perform the procedure while the sensors send data to the computer indicating the current position of each surgical instrument. The computer correlates the data it receives from the instrument-mounted sensors with the digital map that was created from the preoperative tomographic scan. The tomographic scan images are displayed on a video monitor along with an indicator (e.g., cross hairs or an illuminated dot, etc.) showing the real time position of each surgical instrument relative to the anatomical structures shown in the scan images. In this manner, the surgeon is able to know the precise position of each sensor-equipped instrument by viewing the video monitor even if the surgeon is unable to directly visualize the instrument itself at its current location within the body.

Examples of electromagnetic IGS systems that may be used in ENT and sinus surgery include the InstaTrak ENT™ systems available from GE Medical Systems, Salt Lake City, Utah. Other examples of electromagnetic image guidance systems that may be modified for use in accordance with the present disclosure include but are not limited to the CARTO® 3 System by Biosense-Webster, Inc., of Diamond Bar, Calif.; systems available from Surgical Navigation Technologies, Inc., of Louisville, Colo.; and systems available from Calypso Medical Technologies, Inc., of Seattle, Wash.

When applied to functional endoscopic sinus surgery (FESS), balloon sinuplasty, and/or other ENT procedures, the use of image guidance systems allows the surgeon to achieve more precise movement and positioning of the surgical instruments than can be achieved by viewing through an endoscope alone. This is so because a typical endoscopic image is a spatially limited, 2 dimensional, line-of-sight view. The use of image guidance systems provides a real time, 3-dimensional view of all of the anatomy surrounding the operative field, not just that which is actually visible in the spatially limited, 2 dimensional, direct line-of-sight endoscopic view. As a result, image guidance systems may be particularly useful during performance of FESS, balloon sinuplasty, and/or other ENT procedures where a section and/or irrigation source may be desirable, especially in cases where normal anatomical landmarks are not present or are difficult to visualize endoscopically.

While several systems and methods have been made and used in ENT procedures, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

FIG. 3 depicts a detailed side elevational view of the illuminating guide wire of

FIG. 2A;

FIG. 5 depicts a perspective view of an exemplary endoscope suitable for use with the dilation catheter system of FIG. 1;

FIG. 6 depicts a side elevational view of the distal end of the endoscope of FIG. 5, showing an exemplary range of viewing angles;

Figure 1:
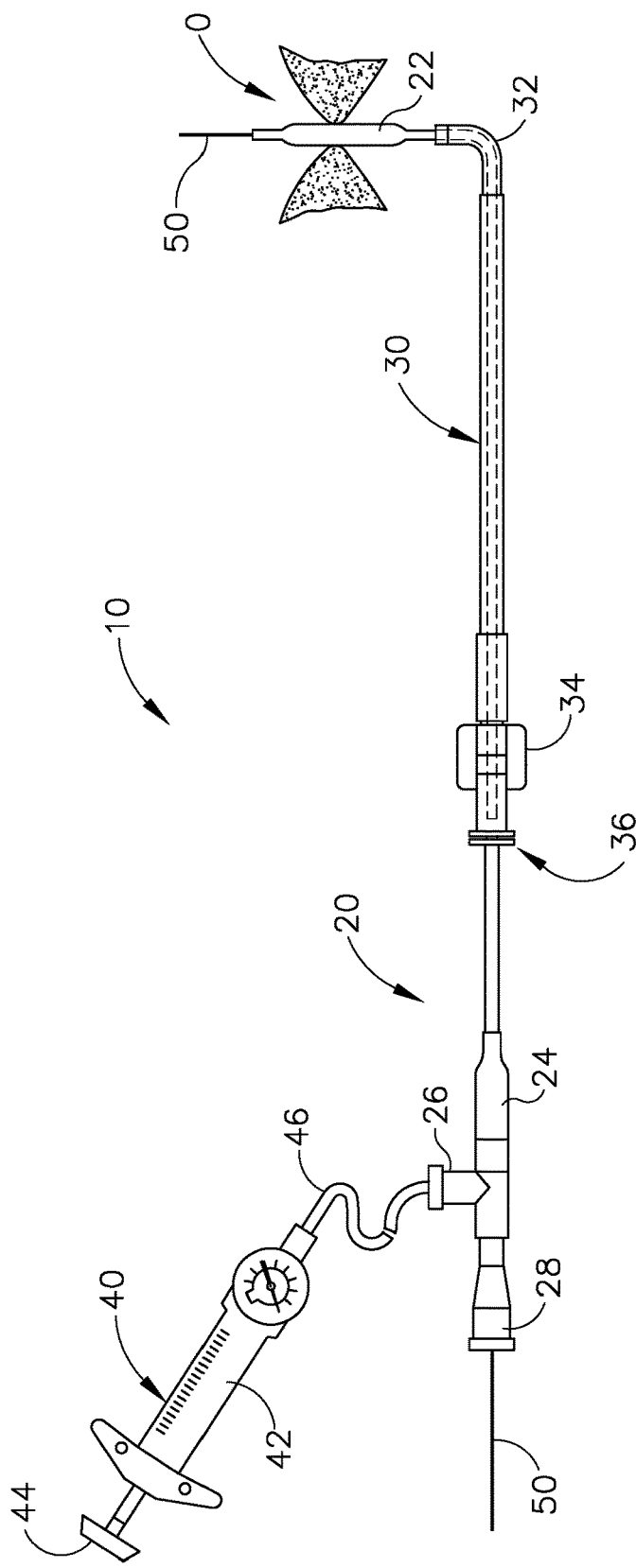
FIG. 1 depicts a side elevational view of an exemplary dilation catheter system.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. For example, while various. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "top" and "bottom" also are used herein with respect to the clinician gripping the handpiece assembly. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Overview of Exemplary Dilation Catheter System

FIG. 1 shows an exemplary dilation catheter system (10) that may be used to dilate the ostium of a paranasal sinus; or to dilate some other anatomical passageway (e.g., within the ear, nose, or throat, etc.). Dilation catheter system (10) of this example comprises a dilation catheter (20), a guide catheter (30), an inflator (40), and a guidewire (50). By way of example only, dilation catheter system (10) may be configured in accordance with at least some of the teachings of U.S. Patent Pub. No. 2011/0004057, now abandoned, the disclosure of which is incorporated by reference herein. In some versions, at least part of dilation catheter system (10) is configured similar to the Relieva® Spin Balloon Sinuplasty™ System by Acclarent, Inc. of Menlo Park, Calif.

Figure 2A:
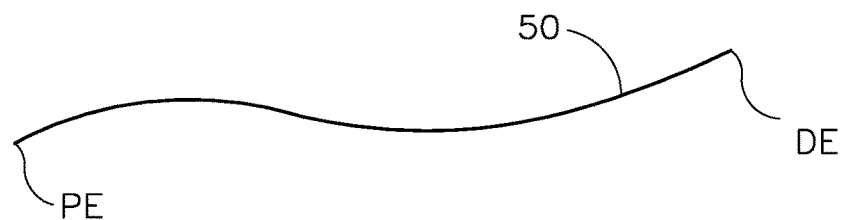
FIG. 2A depicts a side elevational view of an exemplary illuminating guidewire of the dilation catheter system of FIG. 1.
Figure 2B:
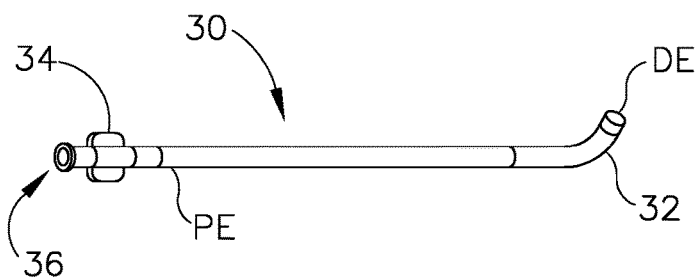
FIG. 2B depicts a side elevational view of an exemplary guide catheter of the dilation catheter system of FIG. 1.
Figure 2C:
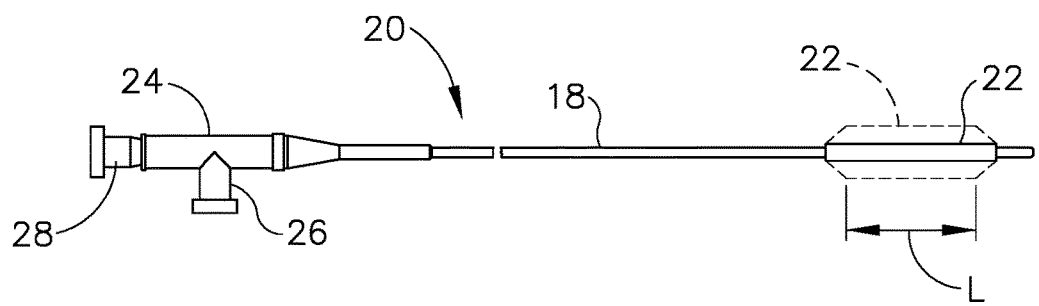
FIG. 2C depicts a side elevational view of an exemplary dilation catheter of the dilation catheter system of FIG. 1.

As best seen in FIG. 2C, the distal end (DE) of dilation catheter (20) includes an inflatable dilator (22). The proximal end (PE) of dilation catheter (20) includes a grip (24), which has a lateral port (26) and an open proximal end (28). A hollow-elongate shaft (18) extends distally from grip. Dilation catheter (20) includes a first lumen (not shown) formed within shaft (18) that provides fluid communication between lateral port (26) and the interior of dilator (22). Dilator catheter (20) also includes a second lumen (not shown) formed within shaft (18) that extends from open proximal end (28) to an open distal end that is distal to dilator (22). This second lumen is configured to slidably receive guidewire (50). The first and second lumens of dilator catheter (20) are fluidly isolated from each other. Thus, dilator (22) may be selectively inflated and deflated by communicating fluid along the first lumen via lateral port (26) while guidewire (50) is positioned within the second lumen. In some versions, dilator catheter (20) is configured similar to the Relieva Ultirra™ Sinus Balloon Catheter by Acclarent, Inc. of Menlo Park, Calif. In some other versions, dilator catheter (20) is configured similar to the Relieva Solo Pro™ Sinus Balloon Catheter by Acclarent, Inc. of Menlo Park, Calif. Other suitable forms that dilator catheter (20) may take will be apparent to those of ordinary skill in the art in view of the teachings herein.

As best seen in FIG. 2B, guide catheter (30) of the present example includes a bent distal portion (32) at its distal end (DE) and a grip (34) at its proximal end (PE). Grip (34) has an open proximal end (36). Guide catheter (30) defines a lumen that is configured to slidably receive dilation catheter (20), such that guide catheter (30) may guide dilator (22) out through bent distal end (32). In some versions, guide catheter (30) is configured similar to the Relieva Flex™ Sinus Guide Catheter by Acclarent, Inc. of Menlo Park, Calif. Other suitable forms that guide catheter (30) may take will be apparent to those of ordinary skill in the art in view of the teachings herein.

Referring back to FIG. 1, inflator (40) of the present example comprises a barrel (42) that is configured to hold fluid and a plunger (44) that is configured to reciprocate relative to barrel (42) to selectively discharge fluid from (or draw fluid into) barrel (42). Barrel (42) is fluidly coupled with lateral port (26) via a flexible tube (46). Thus, inflator (40) is operable to add fluid to dilator (22) or withdraw fluid from dilator (22) by translating plunger (44) relative to barrel (42). In the present example, the fluid communicated by inflator (40) comprises saline, though it should be understood that any other suitable fluid may be used. There are various ways in which inflator (40) may be filled with fluid (e.g., saline, etc.). By way of example only, before flexible tube (46) is coupled with lateral port (26), the distal end of flexible tube (46) may be placed in a reservoir containing the fluid. Plunger (44) may then be retracted from a distal position to a proximal position to draw the fluid into barrel (42). Inflator (40) may then be held in an upright position, with the distal end of barrel (42) pointing upwardly, and plunger (44) may then be advanced to an intermediate or slightly distal position to purge any air from barrel (42). The distal end of flexible tube (46) may then be coupled with lateral port (26). In some versions, inflator (40) is constructed and operable in accordance with at least some of the teachings of U.S. Pub. No. 2014/0074141, entitled "Inflator for Dilation of Anatomical Passageway," published Mar. 13, 2014, issued as U.S. Pat. No. 9,962,530 on May 8, 2018, the disclosure of which is incorporated by reference herein.

Figure 3:
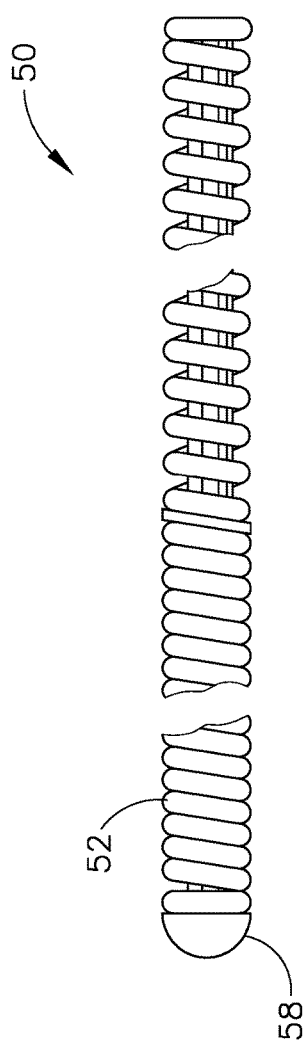
Figure 4:
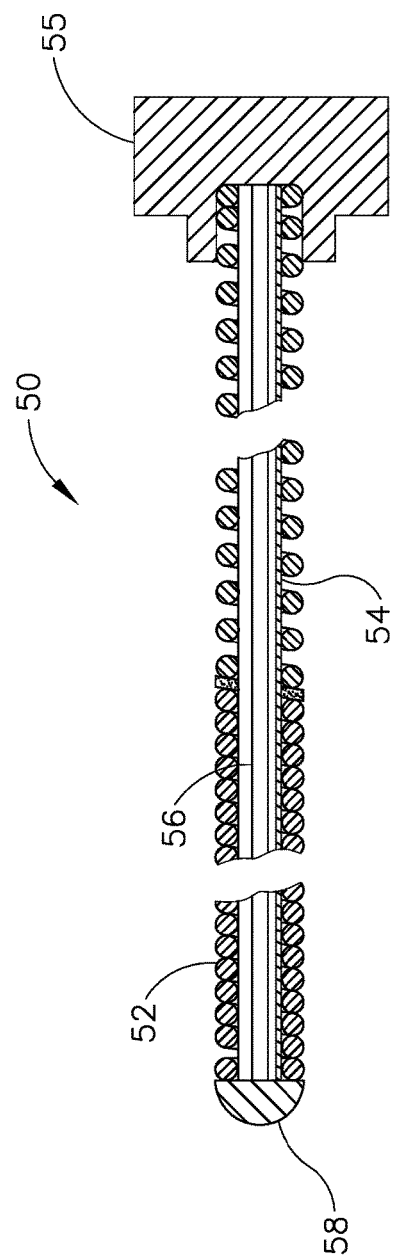
FIG. 4 depicts a detailed side cross-sectional view of the illuminating guidewire of FIG. 2A.

As shown in FIGS. 2A, 3, and 4, guidewire (50) of the present example comprises a coil (52) positioned about a core wire (54). An illumination fiber (56) extends along the interior of core wire (54) and terminates in an atraumatic lens (58). A connector (55) at the proximal end of guidewire (50) enables optical coupling between illumination fiber (56) and a light source (not shown). Illumination fiber (56) may comprise one or more optical fibers. Lens (58) is configured to project light when illumination fiber (56) is illuminated by the light source, such that illumination fiber (56) transmits light from the light source to the lens (58). In some versions, the distal end of guidewire (50) is more flexible than the proximal end of guidewire (50). Guidewire (50) has a length enabling the distal end of guidewire (50) to be positioned distal to dilator (22) while the proximal end of guidewire (50) is positioned proximal to grip (24). Guidewire (50) may include indicia along at least part of its length (e.g., the proximal portion) to provide the operator with visual feedback indicating the depth of insertion of guidewire (50) relative to dilation catheter (20). By way of example only, guidewire (50) may be configured in accordance with at least some of the teachings of U.S. Pub. No. 2012/0078118, issued as U.S. Pat. No. 9,155,492 on Oct. 13, 2015, the disclosure of which is incorporated by reference herein. In some versions, guidewire (50) is configured similar to the Relieva Luma Sentry™ Sinus Illumination System by Acclarent, Inc. of Menlo Park, Calif. Other suitable forms that guidewire (50) may take will be apparent to those of ordinary skill in the art in view of the teachings herein.

II. Overview of Exemplary Endoscope

As noted above, an endoscope (60) may be used to provide visualization within an anatomical passageway (e.g., within the nasal cavity, etc.) during a process of using dilation catheter system (10). As shown in FIGS. 4-5, endoscope of the present example comprises a body (62) and a rigid shaft (64) extending distally from body (62). The distal end of shaft (64) includes a curved transparent window (66). A plurality of rod lenses and light transmitting fibers may extend along the length of shaft (64). A lens is positioned at the distal end of the rod lenses and a swing prism is positioned between the lens and window (66). The swing prism is pivotable about an axis that is transverse to the longitudinal axis of shaft (64). The swing prism defines a line of sight that pivots with the swing prism. The line of sight defines a viewing angle relative to the longitudinal axis of shaft (64). This line of sight may pivot from approximately 0 degrees to approximately 120 degrees, from approximately 10 degrees to approximately 90 degrees, or within any other suitable range. The swing prism and window (66) also provide a field of view spanning approximately 60 degrees (with the line of sight centered in the field of view). Thus, the field of view enables a viewing range spanning approximately 180 degrees, approximately 140 degrees, or any other range, based on the pivot range of the swing prism. Of course, all of these values are mere examples.

Body (62) of the present example includes a light post (70), an eyepiece (72), a rotation dial (74), and a pivot dial (76). Light post (70) is in communication with the light transmitting fibers in shaft (64) and is configured to couple with a source of light, to thereby illuminate the site in the patient distal to window (66). Eyepiece (72) is configured to provide visualization of the view captured through window (66) via the optics of endoscope (60). It should be understood that a visualization system (e.g., camera and display screen, etc.) may be coupled with eyepiece (72) to provide visualization of the view captured through window (66) via the optics of endoscope (60). Rotation dial (74) is configured to rotate shaft (64) relative to body (62) about the longitudinal axis of shaft (64). It should be understood that such rotation may be carried out even while the swing prism is pivoted such that the line of sight is non-parallel with the longitudinal axis of shaft (64). Pivot dial (76) is coupled with the swing prism and is thereby operable to pivot the swing prism about the transverse pivot axis. Indicia (78) on body (62) provide visual feedback indicating the viewing angle. Various suitable components and arrangements that may be used to couple rotation dial (74) with the swing prism will be apparent to those of ordinary skill in the art in view of the teachings herein. By way of example only, endoscope (60) may be configured in accordance with at least some of the teachings of U.S. Pub. No. 2010/0030031, now abandoned, the disclosure of which is incorporated by reference herein. In some versions, endoscope (60) is configured similar to the Acclarent Cyclops™ Multi-Angle Endoscope by Acclarent, Inc. of Menlo Park, Calif. Other suitable forms that endoscope (60) may take will be apparent to those of ordinary skill in the art in view of the teachings herein.

III. Exemplary Method for Dilating the Ostium of a Maxillary Sinus

FIGS. 7A-7E show an exemplary method for using dilation catheter system (10) discussed above to dilate a sinus ostium (O) of a maxillary sinus (MS) of a patient. While the present example is being provided in the context of dilating a sinus ostium (O) of a maxillary sinus (MS), it should be understood that dilation catheter system (10) may be used in various other procedures. By way of example only, dilation catheter system (10) and variations thereof may be used to dilate a Eustachian tube, a larynx, a choana, a sphenoid sinus ostium, one or more openings associated with one or more ethmoid sinus air cells, the frontal recess, and/or other passageways associated with paranasal sinuses. Other suitable ways in which dilation catheter system (10) may be used will be apparent to those of ordinary skill in the art in view of the teachings herein.

Figure 7A:
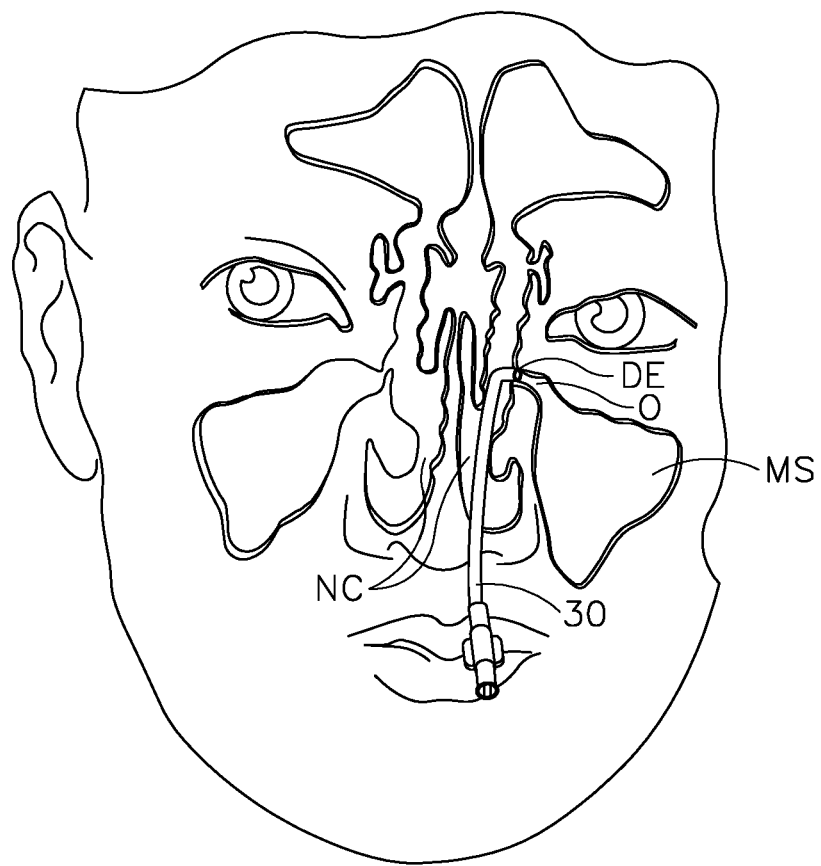
FIG. 7A depicts a front view of the guide catheter of FIG. 2B positioned adjacent an ostium of the maxillary sinus.
Figure 7C:
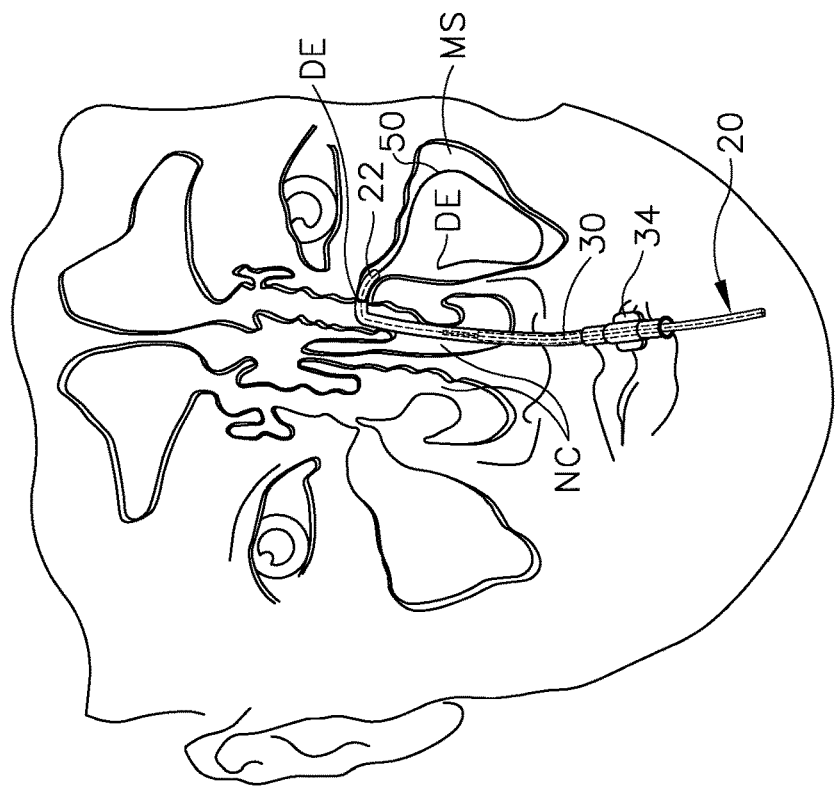
FIG. 7C depicts a front view of the guide catheter of FIG. 2B positioned adjacent an ostium of the maxillary sinus, with the illuminating guidewire of FIG. 2A translated further distally relative to the guide catheter and into the maxillary sinus.
Figure 7B:
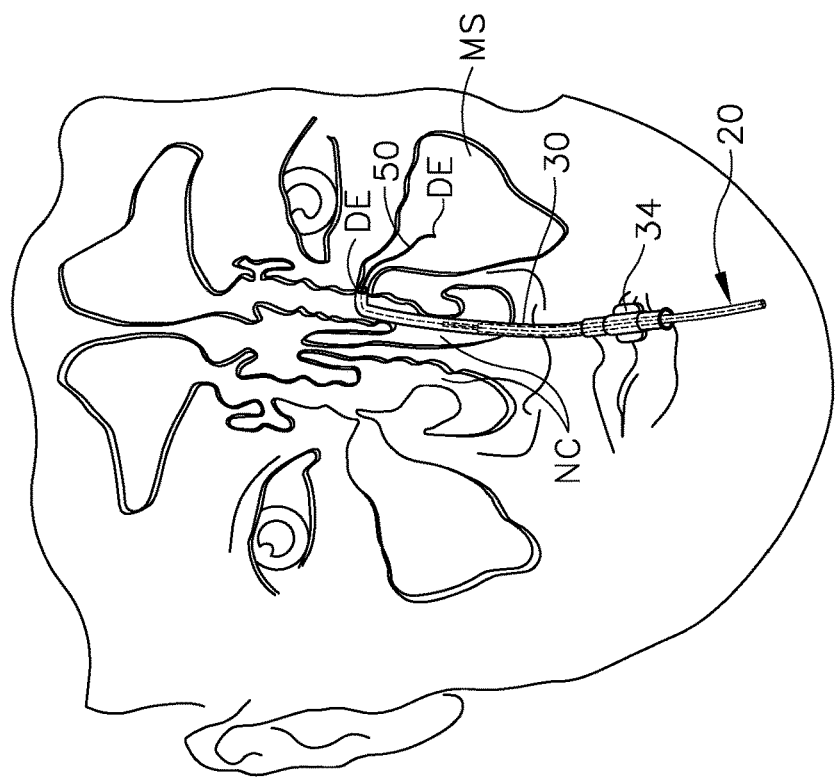
FIG. 7B depicts a front view of the guide catheter of FIG. 2B positioned adjacent an ostium of the maxillary sinus, with the dilation catheter of FIG. 2C and the illuminating guidewire of FIG. 2A positioned in the guide catheter and a distal portion of the guidewire positioned in the maxillary sinus.

In the procedure of the present example, guide catheter (30) may be inserted transnasally and advanced through the nasal cavity (NC) to a position within or near the targeted anatomical passageway to be dilated, the sinus ostium (O), as shown in FIG. 7A. Inflatable dilator (22) and the distal end of guidewire (50) may be positioned within or proximal to bent distal end (32) of guide catheter (30) at this stage. This positioning of guide catheter (30) may be verified endoscopically with an endoscope such as endoscope (60) described above and/or by direct visualization, radiography, and/or by any other suitable method. After guide catheter (30) has been positioned, the operator may advance guidewire (50) distally through guide catheter (30) such that a distal portion of the guidewire (50) passes through the ostium (O) of the maxillary sinus (MS) and into the cavity of the maxillary sinus (MS) as shown in FIGS. 7B and 7C. The operator may illuminate illumination fiber (56) and lens (58), which may provide transcutaneous illumination through the patient's face to enable the operator to visually confirm positioning of the distal end of guidewire (50) in the maxillary sinus (MS) with relative ease.

Figure 7E:
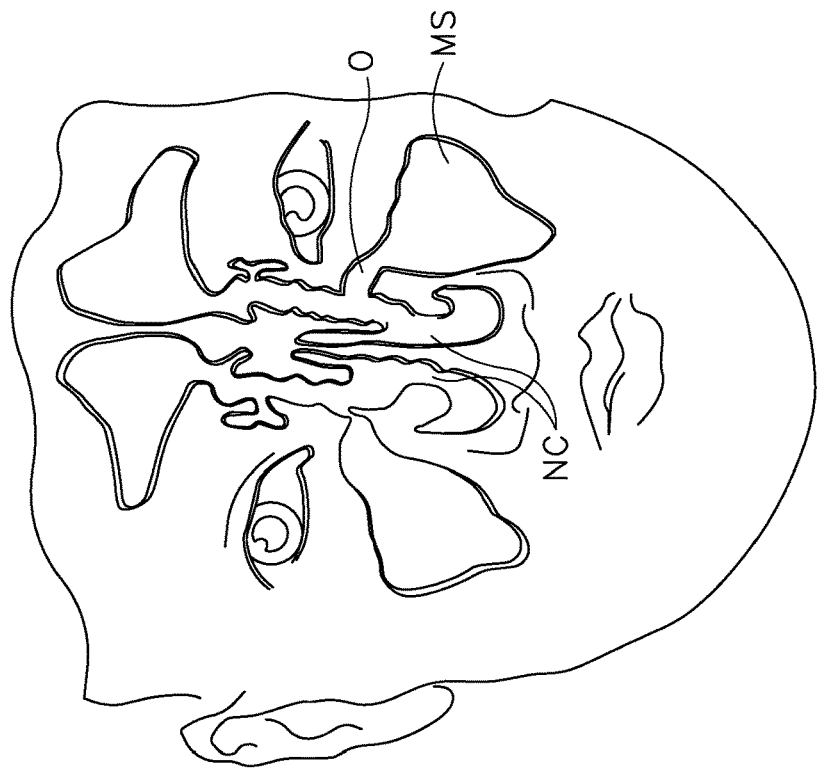
FIG. 7E depicts a front view of an ostium of the maxillary sinus, with the ostium having been enlarged by inflation of the balloon of FIG. 7D.
Figure 7D:
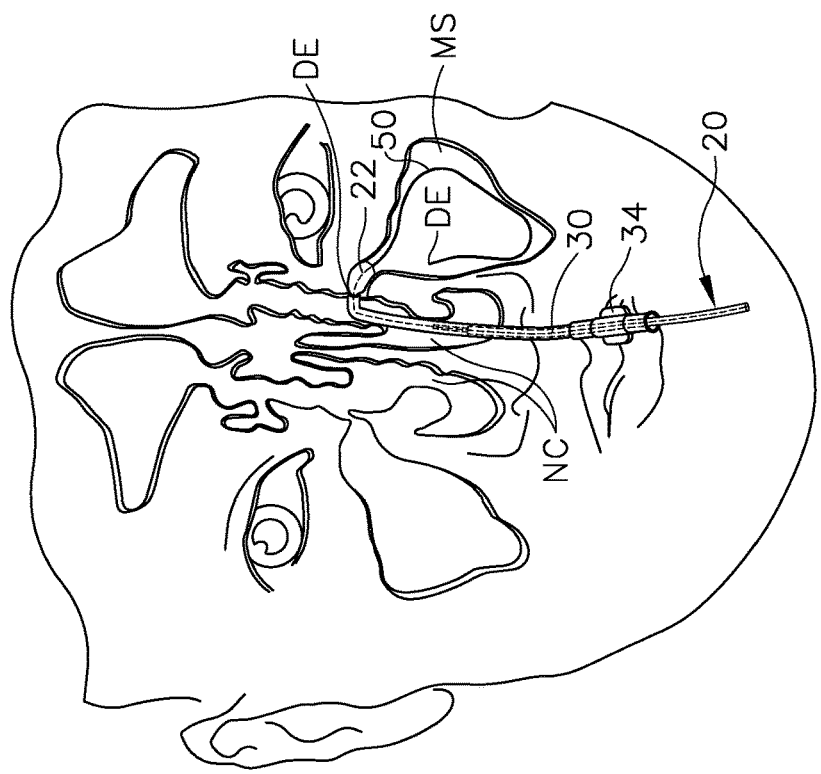
FIG. 7D depicts a front view of the guide catheter of FIG. 2B positioned adjacent an ostium of the maxillary sinus, with the dilation catheter of FIG. 2C translated distally relative to the guide catheter along the illuminating guidewire of FIG. 2A so as to position a balloon of the dilation catheter within the ostium.

As shown in FIG. 7C, with guide catheter (30) and guidewire (50) suitably positioned, dilation catheter (20) is advanced along guidewire (50) and through bent distal end (32) of guide catheter (30), with dilator (22) in a non-dilated state until dilator (22) is positioned within the ostium (O) of the maxillary sinus (MS) (or some other targeted anatomical passageway). After dilator (22) has been positioned within the ostium (O), dilator (22) may be inflated, thereby dilating the ostium (O), as shown in FIG. 7D. To inflate dilator (22), plunger (44) may be actuated to push saline from barrel (42) of inflator (40) through dilation catheter (20) into dilator (22). The transfer of fluid expands dilator (22) to an expanded state to open or dilate the ostium (O), such as by remodeling the bone, etc., forming ostium (O). By way of example only, dilator (22) may be inflated to a volume sized to achieve about 10 to about 12 atmospheres. Dilator (22) may be held at this volume for a few seconds to sufficiently open the ostium (O) (or other targeted anatomical passageway). Dilator (22) may then be returned to a non-expanded state by reversing plunger (44) of inflator (40) to bring the saline back to inflator (40). Dilator (22) may be repeatedly inflated and deflated in different ostia and/or other targeted anatomical passageways. Thereafter, dilation catheter (20), guidewire (50), and guide catheter (30) may be removed from the patient as shown in FIG. 7E.

In some instances, it may be desirable to irrigate the sinus and paranasal cavity after dilation catheter (20) has been used to dilate the ostium (O). Such irrigation may be performed to flush out blood, etc. that may be present after the dilation procedure. For example, in some cases, guide catheter (30) may be allowed to remain in place after removal of guidewire (50) and dilation catheter (20) and a lavage fluid, other substance, or one or more other devices (e.g., lavage catheters, balloon catheters, cutting balloons, cutters, chompers, rotating cutters, rotating drills, rotating blades, sequential dilators, tapered dilators, punches, dissectors, burs, non-inflating mechanically expandable members, high frequency mechanical vibrators, dilating stents and radiofrequency ablation devices, microwave ablation devices, laser devices, snares, biopsy tools, scopes, and devices that deliver diagnostic or therapeutic agents) may be passed through guide catheter (30) for further treatment of the condition. By way of example only, irrigation may be carried out in accordance with at least some of the teachings of U.S. Pub. No. 2008/0183128 pulished Jul. 31, 2008, entitled "Methods, Devices and Systems for Treatment and/or Diagnosis of Disorders of the Ear, Nose and Throat," the disclosure of which is incorporated by reference herein. An example of an irrigation catheter that may be fed through guide catheter (30) to reach the irrigation site after removal of dilation catheter (20) is the Relieva Vortex® Sinus Irrigation Catheter by Acclarent, Inc. of Menlo Park, Calif. Another example of an irrigation catheter that may be fed through guide catheter (30) to reach the irrigation site after removal of dilation catheter (20) is the Relieva Ultirra® Sinus Irrigation Catheter by Acclarent, Inc. of Menlo Park, Calif. Of course, irrigation may be provided in the absence of a dilation procedure; and a dilation procedure may be completed without also including irrigation.

IV. Exemplary Image Guided Surgery Navigation System

Figure 8:
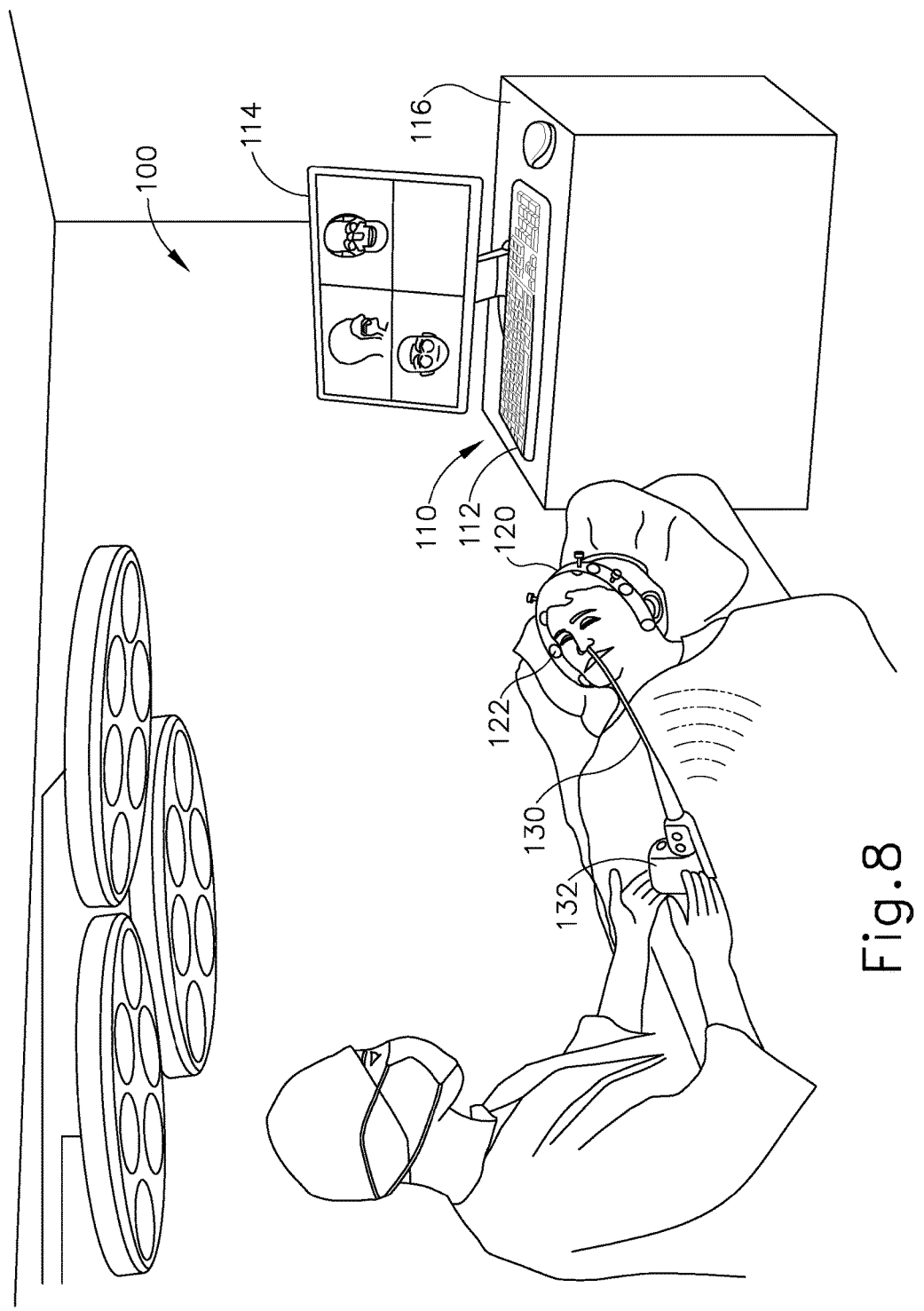
FIG. 8 depicts a schematic view of an exemplary sinus surgery navigation system.

FIG. 8 shows an exemplary IGS navigation system (100) whereby an ENT procedure may be performed using IGS. In some instances, IGS navigation system (100) is used during a procedure where dilation catheter system (10) that may be used to dilate the ostium of a paranasal sinus; or to dilate some other anatomical passageway (e.g., within the ear, nose, or throat, etc.). However, it should be understood that IGS navigation system (100) may be readily used in various other kinds of procedures.

In addition to or in lieu of having the components and operability described herein IGS navigation system (100) may be constructed and operable in accordance with at least some of the teachings of U.S. Pat. No. 8,702,626, entitled "Guidewires for Performing Image Guided Procedures," issued Apr. 22, 2014, the disclosure of which is incorporated by reference herein; U.S. Pat. No. 8,320,711, entitled "Anatomical Modeling from a 3-D Image and a Surface Mapping," issued Nov. 27, 2012, the disclosure of which is incorporated by reference herein; U.S. Pat. No. 8,190,389, entitled "Adapter for Attaching Electromagnetic Image Guidance Components to a Medical Device," issued May 29, 2012, the disclosure of which is incorporated by reference herein; U.S. Pat. No. 8,123,722, entitled "Devices, Systems and Methods for Treating Disorders of the Ear, Nose and Throat," issued Feb. 28, 2012, the disclosure of which is incorporated by reference herein; and U.S. Pat. No. 7,720,521, entitled "Methods and Devices for Performing Procedures within the Ear, Nose, Throat and Paranasal Sinuses," issued May 18, 2010, the disclosure of which is incorporated by reference herein.

Similarly, in addition to or in lieu of having the components and operability described herein, IGS navigation system (100) may be constructed and operable in accordance with at least some of the teachings of U.S. Pat. Pub. No. 2014/0364725, entitled "Systems and Methods for Performing Image Guided Procedures within the Ear, Nose, Throat and Paranasal Sinuses," published Dec. 11, 2014, now abandoned, the disclosure of which is incorporated by reference herein; U.S. Pat. Pub. No. 2014/0200444, entitled "Guidewires for Performing Image Guided Procedures," published Jul. 17, 2014, now abandoned, the disclosure of which is incorporated by reference herein; U.S. Pat. Pub. No. 2012/0245456, entitled "Adapter for Attaching Electromagnetic Image Guidance Components to a Medical Device," published Sep. 27, 2012, issued as U.S. Pat. No. 9,198,736 on Dec. 1, 2015, the disclosure of which is incorporated by reference herein; U.S. Pat. Pub. No. 2011/0060214, entitled "Systems and Methods for Performing Image Guided Procedures within the Ear, Nose, Throat and Paranasal Sinuses," published Mar. 10, 2011, now abandoned, the disclosure of which is incorporated by reference herein; U.S. Pat. Pub. No. 2008/0281156, entitled "Methods and Apparatus for Treating Disorders of the Ear Nose and Throat," published Nov. 13, 2008, issued as U.S. Pat. No. 9,167,961 on Oct. 27, 2015, the disclosure of which is incorporated by reference herein; and U.S. Pat. Pub. No. 2007/0208252, entitled "Systems and Methods for Performing Image Guided Procedures within the Ear, Nose, Throat and Paranasal Sinuses," published Sep. 6, 2007, now abandoned, the disclosure of which is incorporated by reference herein.

Figure 9:
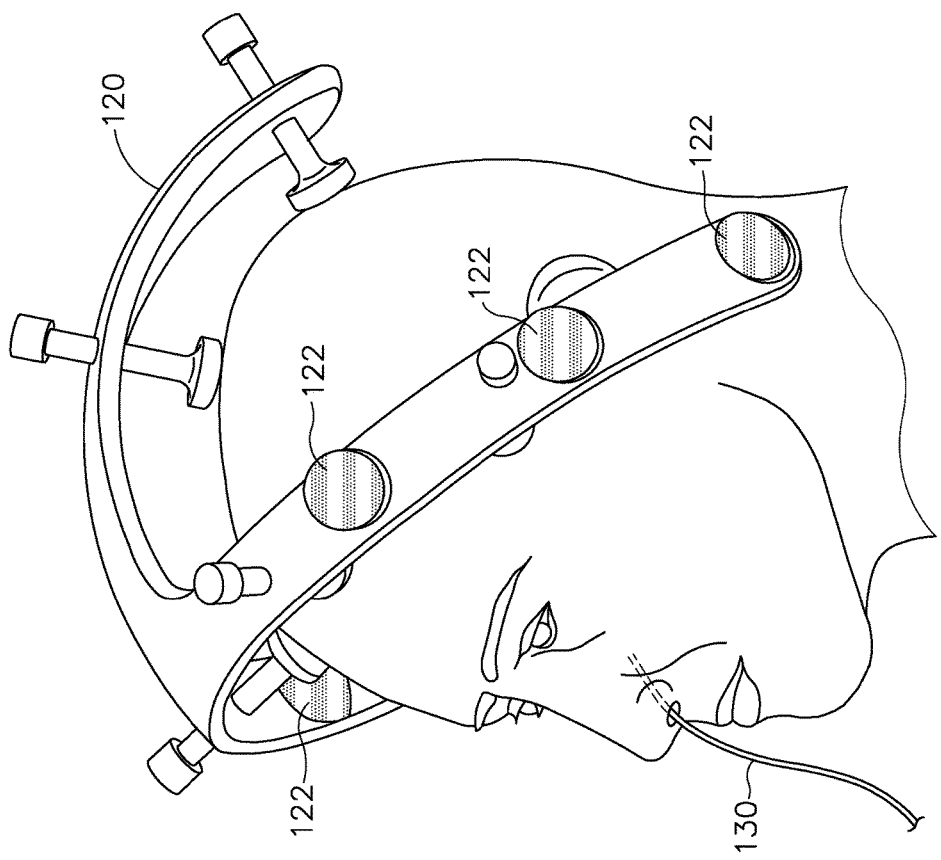
FIG. 9 depicts a perspective view of the head of a patient, with components of the navigation system of FIG. 8.

IGS navigation system (100) of the present example comprises a set of magnetic field generators (122). Before a surgical procedure begins, field generators (122) are fixed to the head of the patient. As best seen in FIG. 9, field generators (122) are incorporated into a frame (120), which is clamped to the head of the patient. While field generators (122) are secured to the head of the patient in this example, it should be understood that field generators (122) may instead be positioned at various other suitable locations and on various other suitable structures. By way of example only, field generators (122) may be mounted on an independent structure that is fixed to a table or chair on which the patient is positioned, on a floor-mounted stand that has been locked in position relative to the head of the patient, and/or at any other suitable location(s) and/or on any other suitable structure(s).

Field generators (122) are operable to generate an electromagnetic field around the head of the patient. In particular, field generators (122) are operated so as to transmit alternating magnetic fields of different frequencies into a region in proximity to frame (120). Field generators (122) thereby enable tracking of the position of a navigation guidewire (130) that is inserted into a nasal sinus of the patient and in other locations within the patient's head. Various suitable components that may be used to form and drive field generators (122) will be apparent to those of ordinary skill in the art in view of the teachings herein.

Navigation guidewire (130) may be used as a substitute for guidewire (50) described above, and may include a sensor (not shown) that is responsive to movement within the fields generated by field generators (122). In particular, signals generated by the sensor of navigation guidewire (130) may be processed by processor (110) to determine the three-dimensional location of navigation guidewire (130) within the patient. Various suitable forms that the sensor may take will be apparent to those of ordinary skill in the art in view of the teachings herein, particularly in view of several of the references that are cited herein in the context of IGS navigation system (100). It should be understood that, when used as a substitute for guidewire (50) in dilation catheter system (10), navigation guidewire (130) may facilitate navigation of instrumentation of dilation catheter system (10) within the patient during performance of a procedure to dilate the ostium of a paranasal sinus; or to dilate some other anatomical passageway (e.g., within the ear, nose, or throat, etc.). It should also be understood that other components of dilation catheter system (10) may incorporate a sensor like the sensor of navigation guidewire (130), including but not limited to the exemplary alternative dilation catheter (200) described below.

IGS navigation system (100) of the present example further comprises a processor (110), which controls field generators (122) and other elements of IGS navigation system (100). Processor (110) comprises a processing unit communicating with one or more memories. Processor (110) of the present example is mounted in a console (116), which comprises operating controls (112) that include a keypad and/or a pointing device such as a mouse or trackball. A physician uses operating controls (112) to interact with processor (110) while performing the surgical procedure.

Console (116) also connects to other elements of system (100). For instance, as shown in FIG. 8 a coupling unit (132) is secured to the proximal end of navigation guidewire (130). Coupling unit (132) of this example is configured to provide wireless communication of data and other signals between console (116) and navigation guidewire (130). In some versions, coupling unit (132) simply communicates data or other signals from navigation guidewire (130) to console (116) uni-directionally, without also communicating data or other signals from console (116). In some other versions, coupling unit (132) provides bidirectional communication of data or other signals between navigation guidewire (130) to console (116). While coupling unit (132) of the present example couples with console (116) wirelessly, some other versions may provide wired coupling between coupling unit (132) and console (116). Various other suitable features and functionality that may be incorporated into coupling unit (132) will be apparent to those of ordinary skill in the art in view of the teachings herein.

Processor (110) uses software stored in a memory of processor (110) to calibrate and operate system (100). Such operation includes driving field generators (122), processing data from navigational guidewire (130), processing data from operating controls (112), and driving display screen (114). The software may be downloaded to processor (110) in electronic form, over a network, for example, or it may, alternatively or additionally, be provided and/or stored on non-transitory tangible media, such as magnetic, optical, or electronic memory.

Processor (110) is further operable to provide video in real time via display screen (114), showing the position of the distal end of navigational guidewire (130) in relation to a video camera image of the patient's head, a CT scan image of the patient's head, and/or a computer generated three-dimensional model of the anatomy within and adjacent to the patient's nasal cavity. Display screen (114) may display such images simultaneously and/or superimposed on each other. Moreover, display screen (114) may display such images during the surgical procedure. Such displayed images may also include graphical representations of instruments that are inserted in the patient's head, such as navigational guidewire (130), such that the operator may view the virtual rendering of the instrument at its actual location in real time. Such graphical representations may actually look like the instrument or may be a much simpler representation such as a dot, crosshairs, etc. By way of example only, display screen (114) may provide images in accordance with at least some of the teachings of U.S. Pub. No. 2016/0008083, entitled "Guidewire Navigation for Sinuplasty," published Jan. 14, 2016, the disclosure of which is incorporated by reference herein. In the event that the operator is also using an endoscope, the endoscopic image may also be provided on display screen (114). The images provided through display screen (114) may help guide the operator in maneuvering and otherwise manipulating instruments within the patient's head.

In the present example, navigational guidewire (130) includes one or more coils at the distal end of navigational guidewire (130). Such a coil serves as a sensor as referred to above. When such a coil is positioned within an electromagnetic field generated by field generators (122), movement of the coil within that magnetic field may generate electrical current in the coil, and this electrical current may be communicated along the electrical conduit(s) in navigational guidewire (130) and further to processor (110) via coupling unit (132). This phenomenon may enable IGS navigation system (00) to determine the location of the distal end of navigational guidewire (130) within a three-dimensional space as will be described in greater detail below. In particular, processor (110) executes an algorithm to calculate location coordinates of the distal end of navigational guidewire (130) from the position related signals of the coil(s) in navigational guidewire (130).

In some instances, navigational guidewire (130) is used to generate a three-dimensional model of the anatomy within and adjacent to the patient's nasal cavity; in addition to being used to provide navigation for dilation catheter system (100) within the patient's nasal cavity. Alternatively, any other suitable device may be used to generate a three-dimensional model of the anatomy within and adjacent to the patient's nasal cavity before navigational guidewire (130) is used to provide navigation for dilation catheter system (100) within the patient's nasal cavity. By way of example only, a model of this anatomy may be generated in accordance with at least some of the teachings of U.S. patent application Ser. No. 14/825,551, entitled "System and Method to Map Structures of Nasal Cavity," filed Aug. 13, 2015, issued as U.S. Pat. No. 10,362,965 on Jul. 30, 2019, the disclosure of which is incorporated by reference herein. Still other suitable ways in which a three-dimensional model of the anatomy within and adjacent to the patient's nasal cavity may be generated will be apparent to those of ordinary skill in the art in view of the teachings herein. It should also be understood that, regardless of how or where the three-dimensional model of the anatomy within and adjacent to the patient's nasal cavity is generated, the model may be stored on console (116). Console (116) may thus render images of at least a portion of the model via display screen (114) and further render real-time video images of the position of navigational guidewire (130) in relation to the model via display screen (114).

V. Exemplary Alternative Dilation Catheter

In some instances, the tissue of a dilated anatomical passageway (e.g., sinus ostium or other passageway associated with drainage of a paranasal sinus, a Eustachian tube, etc.) may become diseased, may become swollen, may naturally grow, or may develop some other condition that might adversely impact the patency of the dilated passageway. If this occurs, the adverse impact of the patency on the dilated passageway might frustrate the purpose of the dilation procedure. It may therefore be desirable to supplement the dilation procedure with a treatment that will reduce the likelihood that the tissue of the dilated anatomical passageway will become diseased, become swollen, grow, or develop some other condition that might adversely impact the patency of the dilated passageway.

In some cases, applying RF energy to the tissue of the dilated anatomical passageway may reduce the likelihood that the tissue of the dilated anatomical passageway will become diseased, become swollen, grow, or develop some other condition that might adversely impact the patency of the dilated passageway. In particular, the RF energy may ablate the tissue and thereby generate a scar that will not become diseased, become swollen, grow, or develop some other condition that might adversely impact the patency of the dilated passageway. In other words, the RF-generated scar may help maintain patency of the dilated anatomical passageway. Moreover, the RF ablation may immediately stop bleeding that might otherwise occur as a result of a dilation procedure.

In addition, it may be beneficial to apply drugs or some other media (e.g., antibiotics, etc.) to the tissue of the dilated anatomical passageway. Such drugs may be applied in conjunction with the RF energy. The following description relates to an exemplary device that may be used to apply RF energy, and in some cases drugs and/or other media, to the tissue of an anatomical passageway before, during, and/or after a dilation procedure.

FIGS. 10-12B show an exemplary alternative dilation catheter (200). It should be understood that dilation catheter (200) may be used with dilation catheter system (10) in place of dilation catheter (20). Other suitable devices with which dilation catheter (200) may be used will be apparent to those of ordinary skill in the art in view of the teachings herein. Dilation catheter (200) of this example comprises a shaft (202), an inflatable dilator (210), and a wire assembly (220). Dilator (210) and wire assembly (220) are both fixedly secured to shaft (202). Dilation catheter (200) of the present example is also in communication with an inflator (204), an RF power source (206), and a navigation system (208).

Figure 12A:
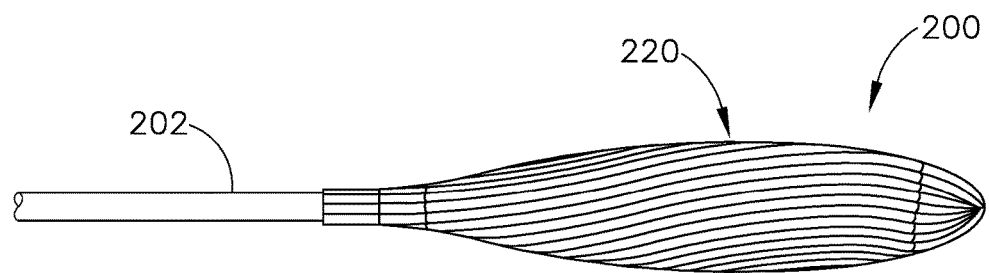
FIG. 12A depicts a side elevational view of the distal end of the dilator of FIG. 10, with the dilator in a non-expanded state.
Figure 12B:
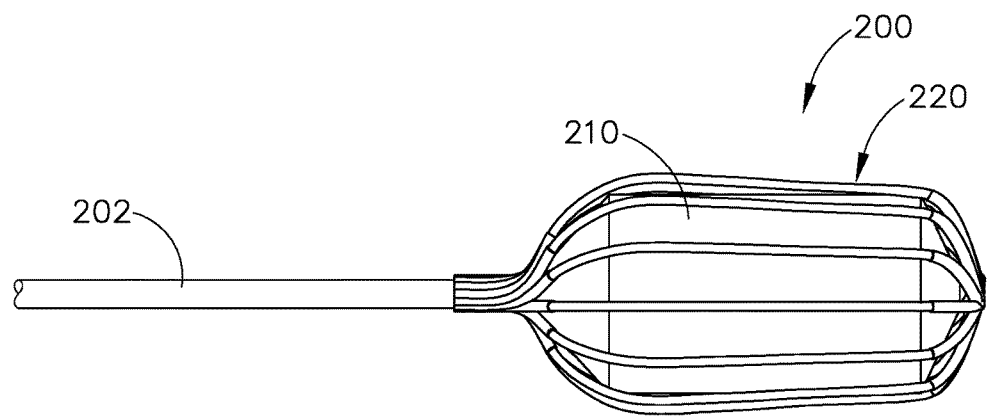
FIG. 12B depicts a side elevational view of the distal end of the dilator of FIG. 10, with the dilator in an expanded state.

Dilator (210) of the present example is substantially identical to dilator (22) described above, such that dilator (210) is operable to transition between a non-expanded configuration (FIG. 12A) and an expanded configuration (FIG. 12B). To provide such transitioning, dilator (210) is in fluid communication with an inflator (204). Inflator (204) may be constructed and operable just like inflator (40) described above; or may have any other suitable configuration. By way of example only, saline or any other suitable fluid may be used to selectively inflate dilator (210). In the present example, dilator (210) is formed of a non-compliant or non-extensible material, such that dilator (210) will provide a substantially consistent inflated configuration.

Wire assembly (220) is positioned coaxially about dilator (210), such that wire assembly (220) encompasses dilator (210). In the present example, the proximal end of wire assembly (220) is proximal to the proximal end of dilator (210); and the distal end of wire assembly (220) is distal to the distal end of dilator (210). Wire assembly (220) comprises a set of wires (222, 224, 226). By way of example only, wires (222, 224, 226) may be formed of nitinol, silver, and/or any other electrically conductive material (or combination of materials). Wires (222, 224) are electrically coupled with RF power source (206). In particular, RF power source (206) is operable to provide a positive charge to wires (222) and a negative charge to wires (224). It should therefore be understood that wires (222, 224) may cooperate to apply bipolar RF energy to tissue that contacts wires (222, 224). It should also be understood that this bipolar RF energy may scar the tissue as noted above.

Figure 10:
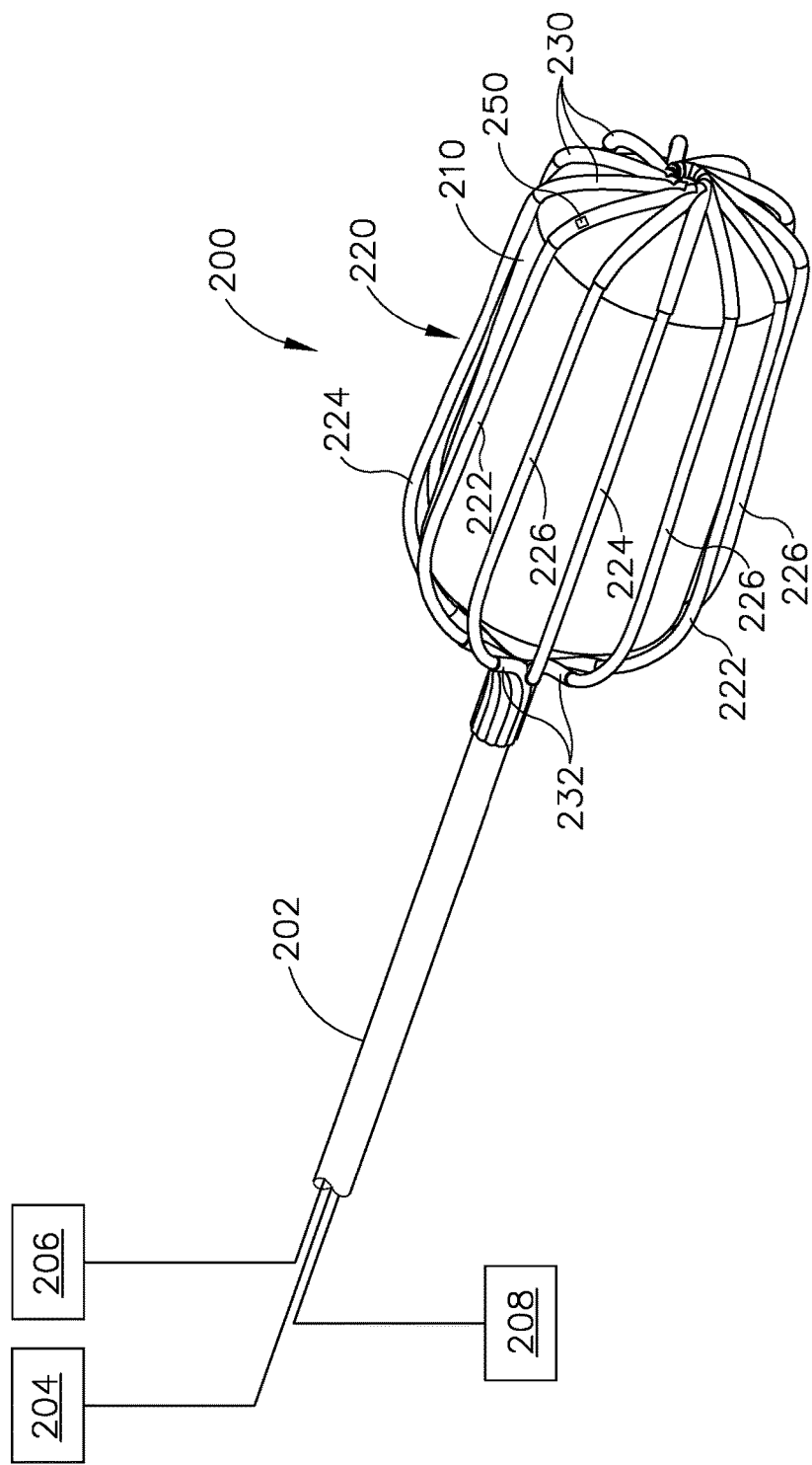
FIG. 10 depicts a perspective view of the distal end of an exemplary alternative dilator that may be used with the dilation catheter system of FIG. 1.
Figure 11:
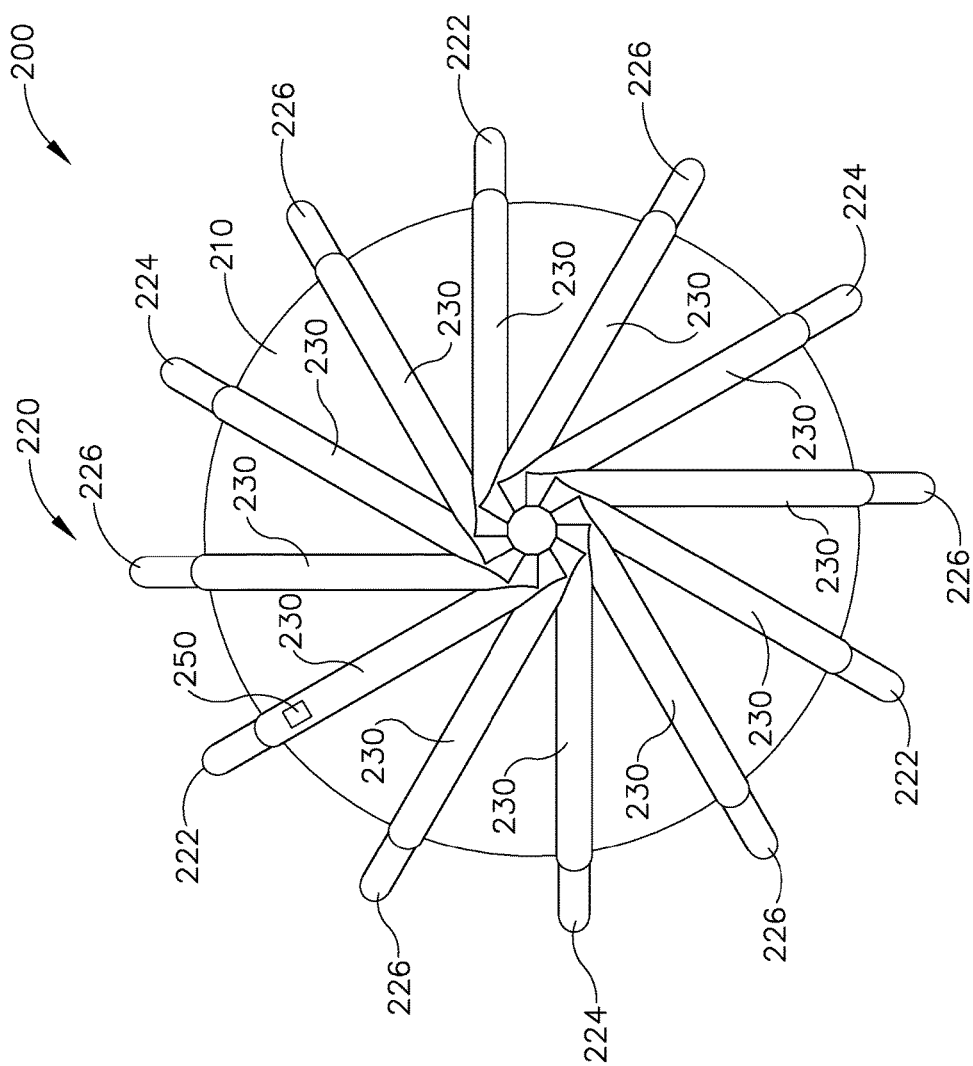
FIG. 11 depicts an end view of the distal end of the dilator of FIG. 10.

Wires (226) are coated with a non-conductive coating in this example, such that wires (226) are electrically non-conductive. Various suitable kinds of non-conductive coatings that may be applied to wires (226) will be apparent to those of ordinary skill in the art in view of the teachings herein. As best seen in FIGS. 10-11, wires (226) are interposed between wires (222, 224), and wires (222, 224) alternate in their positioning between adjacent wires (226). The distal and proximal ends of wires (222, 224, 226) include additional non-conductive coating (230 232) in this example. It should be understood that this additional non-conductive coating (230 232) may prevent short circuits from forming between the distal ends of wires (222, 224) or between the proximal ends of wires (222, 224). While an additional non-conductive coating (230, 232) is applied to the distal and proximal ends of wires (226) in this example, it should be understood that an additional non-conductive coating (230 232) is not necessarily required for wires (226), particularly since the entire length of each wire (226) is already coated with a non-conductive coating in this example.

As shown in FIGS. 12A-12B, wire assembly (220) is operable to expand and contract with dilator (210). In particular, wire assembly (220) is resiliently biased to contract to the non-expanded state shown in FIG. 12A; yet wire assembly (220) is also flexible enough to expand with dilator (210) to achieve the expanded state shown in FIG. 12B, without substantially impeding the expansion of dilator (210). Moreover, the interior lengths of wires (222, 224, 226) are not bonded to dilator (210) it this example, such that wires (222, 224, 226) may slide along the exterior of dilator (210) as dilator (210) transitions between the expanded and non-expanded states. In some versions, wire assembly (220) is resiliently biased to assume a twisted configuration (i.e., twisted about the longitudinal axis of dilation catheter (200)) in the non-expanded state.

In an exemplary use, dilation catheter (200) is positioned such that dilator (210) and wire assembly (220) are located within a targeted anatomical passageway. Dilator (210) is in a non-expanded state (FIG. 12A) during such positioning. By way of example only, the targeted anatomical passageway may comprise an ostium of a paranasal sinus, some other drainage passageway associated with a paranasal sinus, or a Eustachian tube. By way of further example only, dilation catheter (200) may be positioned within the targeted anatomical passageway by using guide catheter (30), guidewire (50), and/or any other suitable instrumentation. Various suitable locations in which dilation catheter (200) may be used, and various suitable ways in which dilation catheter (200) may be guided to such locations, will be apparent to those of ordinary skill in the art in view of the teachings herein.

Once dilator (210) and wire assembly (220) are located within the targeted anatomical passageway, inflator (204) may be activated to expand dilator (210) to the expanded state (FIG. 12B). As noted above, wire assembly (220) expands with dilator (210). The expansion of dilator (210) and wire assembly (220) will dilate the targeted anatomical passageway. While dilator (210) and wire assembly (220) are in the expanded state, RF power source (206) is activated to apply bipolar RF energy via wires (222, 224) to the tissue defining the targeted anatomical passageway. This RF energy generates a scar at the adjacent tissue. In some instances, the operator may alternatingly transition dilator (210) and wire assembly (220) between the expanded and non-expended state several times, applying RF energy any suitable number times when dilator (210) and wire assembly (220) are expanded. The operator may then remove dilation catheter (200) from the patient with dilator (210) and wire assembly (220) in the non-expanded state, resulting in a dilated anatomical passageway with a scar eventually forming at the tissue defining the dilated anatomical passageway.

In some variations, dilator (210) and/or wire assembly (220) is coated with a drug and/or other media (e.g., antibiotic, etc.), such that dilator (210) and/or wire assembly (220) may apply such a drug and/or other media to the tissue. As with the RF energy, the drug and/or other media may be delivered to the tissue as dilator (210) is dilating the targeted anatomical passageway. In some of these variations, the RF energy may be used to assist in the delivery of the drug and/or other media to the tissue. In particular, wires (222, 224) may be used to transmit high amplitude pulses to provide electroporation in the tissue, which may result in faster and more effective delivery of the drug and/or other media to the tissue. Various suitable ways in which RF power source (206) and wires (222, 224) may be used to provide such electroporation will be apparent to those of ordinary skill in the art in view of the teachings herein. It should be understood that this aspect of electroporation is merely optional. Likewise, the aspect of delivering a drug or other media to the tissue is merely optional.

As noted above, dilation catheter (200) is also in communication with navigation system (208). Navigation system (208) of this example may be configured and operable just like IGS navigation system (100) described above. As shown in FIGS. 10-11, dilation catheter (200) of the present example comprises a sensor (250) that is configured to cooperate with navigation system (208) to generate position related data through navigation system (208), thereby enabling the operator to determine the precise location of dilation catheter (200) within the patient as described above in the context of IGS navigation system (100). While sensor (250) is shown as being located on wire (222), it should be understood that sensor (250) may be positioned elsewhere on dilation catheter (200). By way of example only, sensor (250) may be in the form of a coil that generates an electrical current when dilation catheter (200) is moved within an electromagnetic field, and this electrical current may be processed by navigation system (208) to determine the location of sensor (250) within a three-dimensional space as described above.

In versions where dilation catheter (200) includes a sensor (250), it should be understood that sensor (250) may be used in various anatomical locations without wire assembly (220) necessarily applying RF energy within such anatomical locations. In other words, the navigational functionality provided by sensor (250) may be utilized completely independently of the RF ablation functionality provided by wire assembly (220). It should also be understood that sensor (250) and navigation system (208) are merely optional, such that sensor (250) and navigation system (208) may be omitted if desired.

VI. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

An apparatus comprising: (a) a shaft having a proximal end and a distal end; (b) an expandable dilator located at the distal end of the shaft, wherein the expandable dilator is operable to transition between a non-expanded configuration and an expanded configuration, wherein the expandable dilator has a proximal end and a distal end; and (c) a wire assembly, wherein the wire assembly is disposed about an exterior of the expandable dilator, wherein the wire assembly has a proximal end and a distal end, wherein the proximal end of the wire assembly is proximal to the proximal end of the expandable dilator, wherein the distal end of the wire assembly is distal to the distal end of the dilator, wherein the wire assembly is configured to apply bipolar RF energy to tissue.

Example 2

The apparatus of Example 1, wherein the wire assembly comprises a first plurality of wires and a second plurality of wires, wherein the first plurality of wires is configured to provide a first pole of the RF energy, wherein the second plurality of wires is configured to provide a second pole of the RF energy.

Example 3

The apparatus of Example 2, wherein the wire assembly further comprises a third plurality of wires, wherein the third plurality of wires include a non-conductive coating.

Example 4

The apparatus of Example 3, wherein the wires of the third plurality of wires are angularly interposed between the wires of the first and second pluralities of wires.

Example 5

The apparatus of any one or more of Examples 1 through 4, wherein the wire assembly further includes a proximal region including the proximal end of the wire assembly, a distal region including the distal end of the wire assembly, and an intermediate region, wherein the intermediate region includes electrically conductive exposed wires.

Example 6

The apparatus of Example 5, wherein the proximal region includes an electrically insulating coating, wherein the distal region includes an electrically insulating coating.

Example 7

The apparatus of any one or more of Examples 1 through 6, wherein the wire assembly is configured to transition with the expandable dilator between a non-expanded configuration and an expanded configuration.

Example 8

The apparatus of Example 7, wherein the wire assembly is resiliently biased toward the non-expanded configuration.

Example 9

The apparatus of any one or more of Examples 1 through 8, wherein the wire assembly includes wires formed at least in part of nitinol.

Example 10

The apparatus of any one or more of Examples 1 through 9, wherein the wire assembly includes wires formed at least in part of silver.

Example 11

The apparatus of any one or more of Examples 1 through 10, further comprising a drug or other therapeutic substance applied to one or more of the expandable dilator or the wire assembly.

Example 12

The apparatus of Example 11, further comprising an RF energy source coupled with the wire assembly, wherein the RF energy source is configured to apply pulses of RF energy via the wire assembly to thereby provide electroporation in tissue.

Example 13

The apparatus of any one or more of Examples 1 through 12, further comprising a sensor, wherein the sensor is configured to cooperate with a navigation system to generate data indicating a position of one or both of the expandable dilator or the wire assembly within a patient.

Example 14

The apparatus of Example 13, wherein the sensor is located in the wire assembly.

Example 15

The apparatus of any one or more of Examples 1 through 14, wherein the expandable dilator comprises a balloon formed of a non-compliant material.

Example 16

The apparatus of any one or more of Examples 1 through 15, further comprising a fluid source in fluid communication with the expandable dilator.

Example 17

An apparatus comprising: (a) a shaft having a proximal end and a distal end; (b) an expandable dilator located at the distal end of the shaft, wherein the expandable dilator is operable to transition between a non-expanded configuration and an expanded configuration; (c) a wire assembly, wherein the wire assembly is disposed about an exterior of the expandable dilator, wherein the wire assembly comprises: (i) a first plurality of wires, wherein at least a portion of each wire of the first plurality of wires includes an exposed electrically conductive surface, and (ii) a second plurality of wires, wherein at least a portion of each wire of the second plurality of wires includes an exposed electrically conductive surface; and (d) an RF power source in communication with the wire assembly, wherein the first plurality of wires is operable to provide a first polarity of RF energy to tissue based on electrical power from the RF power source, wherein the second plurality of wires is operable to provide a second polarity of RF energy to tissue based on electrical power from the RF power source.

Example 18

The apparatus of Example 17, wherein the first and second plurality of wires are arranged in an alternating angularly spaced array.

Example 19

The apparatus of any one or more of Examples 17 through 18, further comprising a third plurality of wires interposed between the first and second pluralities of wires, wherein each wire of the third plurality of wires is coated with an electrically non-conductive coating along the full length of each wire of the third plurality of wires.

Example 20

A method of treating an anatomical passageway of a patient, comprising: (a) inserting a distal end portion of a dilation catheter into a patient, wherein the dilation catheter comprises a shaft, an expandable dilator, and a wire assembly, wherein the wire assembly is disposed about an exterior of the expandable dilator, wherein the expandable dilator is in a non-expanded state during the act of inserting; (b) positioning the expandable dilator and the wire assembly in an anatomical passageway, wherein the anatomical passageway is selected from the group consisting of a Eustachian tube or a drainage passageway associated with a paranasal sinus, wherein the expandable dilator is in a non-expanded state during the act of positioning; (c) expanding the expandable dilator within the anatomical passageway, thereby dilating the anatomical passageway; and (d) activating the wire assembly with bipolar RF energy, thereby applying bipolar energy to tissue surrounding the anatomical passageway.

VII. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:
1. An apparatus comprising:
(a) a shaft having a proximal end and a distal end and defining a longitudinal axis;
(b) an expandable dilator located at the distal end of the shaft, wherein the expandable dilator is operable to transition between a non-expanded configuration and an expanded configuration, wherein the expandable dilator has a proximal end and a distal end; and
(c) a wire assembly, wherein the wire assembly is disposed about an exterior of the expandable dilator, wherein the wire assembly is configured to transition with the expandable dilator between a non-expanded state and an expanded state, wherein a portion of each wire of the wire assembly is resiliently biased to assume a twisted configuration about the longitudinal axis of the shaft while the expandable dilator is in the non-expanded configuration, wherein the portion of each wire of the wire assembly is configured to be straightened to assume an untwisted configuration about the longitudinal axis of the shaft while the expandable dilator is in the expanded configuration, wherein the wire assembly is configured to apply bipolar RF energy to tissue.

2. The apparatus of claim 1, wherein the wire assembly comprises a first plurality of wires and a second plurality of wires, wherein the first plurality of wires is configured to provide a first pole of the RF energy, wherein the second plurality of wires is configured to provide a second pole of the RF energy.

3. The apparatus of claim 2, wherein the wire assembly has a proximal end and a distal end, wherein each wire of the first plurality of wires and the second plurality of wires includes a tangentially rotatable connector and couples at the distal end of the wire assembly, wherein each wire of the first plurality of wires and the second plurality of wires rotates via the tangentially rotatable connector as the wire assembly transitions between the non-expanded state and the expanded state.

4. The apparatus of claim 2, wherein the wire assembly further comprises a third plurality of wires, wherein the third plurality of wires include a non-conductive coating.

5. The apparatus of claim 4, wherein the wires of the third plurality of wires are angularly interposed between the wires of the first and second pluralities of wires.

6. The apparatus of claim 5, wherein the wire assembly has a proximal end and a distal end, wherein the wire assembly further includes a proximal region including the proximal end of the wire assembly, a distal region including the distal end of the wire assembly, and an intermediate region, wherein the intermediate region includes electrically conductive exposed wires.

7. The apparatus of claim 6, wherein the proximal region includes an electrically insulating coating, wherein the distal region includes an electrically insulating coating.

8. The apparatus of claim 5, wherein the wire assembly is resiliently biased toward the non-expanded state, wherein the expandable dilator transitioning to the expanded configuration results in the wire assembly transitioning to the expanded state.

9. The apparatus of claim 5, wherein the wire assembly includes wires formed at least in part of nitinol.

10. The apparatus of claim 5, wherein the wire assembly includes wires formed at least in part of silver.

11. The apparatus of claim 5, further comprising a drug or other therapeutic substance applied to one or more of the expandable dilator or the wire assembly.

12. The apparatus of claim 11, further comprising an RF energy source coupled with the wire assembly, wherein the RF energy source is configured to apply pulses of RF energy via the wire assembly to thereby provide electroporation in tissue.

13. The apparatus of claim 5, further comprising a sensor, wherein the sensor is configured to cooperate with a navigation system to generate data indicating a position of one or both of the expandable dilator or the wire assembly within a patient.

14. The apparatus of claim 13, wherein the sensor is located in the wire assembly.

15. The apparatus of claim 5, wherein the expandable dilator comprises a balloon formed of a non-compliant material.

16. The apparatus of claim 5, further comprising a fluid source in fluid communication with the expandable dilator.

17. An apparatus comprising:
(a) a shaft having a proximal end and a distal end and defining a longitudinal axis;
(b) an expandable dilator located at the distal end of the shaft, wherein the expandable dilator is operable to transition between a non-expanded configuration and an expanded configuration;
(c) a wire assembly, wherein the wire assembly is disposed about an exterior of the expandable dilator, wherein a portion of each wire of the wire assembly is resiliently biased to assume a twisted configuration about the longitudinal axis of the shaft while the expandable dilator is in the non-expanded configuration, wherein the portion of each wire of the wire assembly is configured to be straightened to assume an untwisted configuration about the longitudinal axis of the shaft while the expandable dilator is in the expanded configuration, wherein the wire assembly comprises:
(i) a first plurality of wires, wherein at least a portion of each wire of the first plurality of wires includes an exposed electrically conductive surface, and
(ii) a second plurality of wires, wherein at least a portion of each wire of the second plurality of wires includes an exposed electrically conductive surface; and
(d) an RF power source in communication with the wire assembly, wherein the first plurality of wires is operable to provide a first polarity of RF energy to tissue based on electrical power from the RF power source, wherein the second plurality of wires is operable to provide a second polarity of RF energy to tissue based on electrical power from the RF power source.

18. The apparatus of claim 17, wherein the first and second plurality of wires are arranged in an alternating angularly spaced array.

19. The apparatus of claim 17, further comprising a third plurality of wires interposed between the first and second pluralities of wires, wherein each wire of the third plurality of wires is coated with an electrically non-conductive coating along the full length of each wire of the third plurality of wires.

20. A method of treating an anatomical passageway of a patient, comprising:
(a) inserting a distal end portion of a dilation catheter into a patient, wherein the dilation catheter comprises a shaft, an expandable dilator, and a wire assembly, wherein the wire assembly is disposed about an exterior of the expandable dilator, wherein the expandable dilator is in a non-expanded state during the act of inserting, wherein each wire of the wire assembly is in a twisted configuration about a longitudinal axis defined by the shaft;

(b) positioning the expandable dilator and the wire assembly in an anatomical passageway, wherein the anatomical passageway is selected from the group consisting of a Eustachian tube or a drainage passageway associated with a paranasal sinus, wherein the expandable dilator is in the non-expanded state and each wire of the wire assembly is in the twisted configuration during the act of positioning;

(c) expanding the expandable dilator within the anatomical passageway and straightening at least a portion of each wire of the wire assembly to assume an untwisted configuration, thereby dilating the anatomical passageway; and (d) activating the wire assembly with bipolar RF energy, thereby applying bipolar energy to tissue surrounding the anatomical passageway.

* * * * *